United States Patent
Carney et al.

(10) Patent No.: US 7,473,230 B2
(45) Date of Patent: Jan. 6, 2009

(54) INSTRUMENTED CATHETER WITH DISTANCE COMPENSATION TO SENSE VULNERABLE PLAQUE

(75) Inventors: James Kevin Carney, Eden Praire, MN (US); David L. Thompson, Andover, MN (US); Mark Brister, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 116 days.

(21) Appl. No.: 11/676,604

(22) Filed: Feb. 20, 2007

(65) Prior Publication Data

US 2007/0142726 A1   Jun. 21, 2007

Related U.S. Application Data

(62) Division of application No. 10/692,145, filed on Oct. 22, 2003, now Pat. No. 7,195,599.

(51) Int. Cl.
*A61B 5/00* (2006.01)

(52) U.S. Cl. .................. 600/549; 600/481; 600/587

(58) Field of Classification Search .................. 600/481, 600/549, 587
See application file for complete search history.

(56) References Cited

U.S. PATENT DOCUMENTS

| | | | |
|---|---|---|---|
| 5,840,030 | A | 11/1998 | Ferek-Petric et al. |
| 5,935,075 | A | 8/1999 | Casscells et al. |
| 6,178,346 | B1 | 1/2001 | Amundson et al. |
| 6,366,799 | B1 | 4/2002 | Acker et al. |
| 6,536,949 | B1 | 3/2003 | Heuser |
| 6,615,071 | B1 | 9/2003 | Casscells et al. |
| 2003/0120171 | A1 | 6/2003 | Diamantopoulos et al. |
| 2003/0176810 | A1 | 9/2003 | Maahs et al. |
| 2003/0199768 | A1 | 10/2003 | Despedes et al. |

*Primary Examiner*—Max Hindenburg
*Assistant Examiner*—Sean P Dougherty (57) ABSTRACT

A method and apparatus for determining vulnerable plaque in a cardiovascular lumen is disclosed. In one embodiment, a guide member comprising a temperature sensor and a distance sensor are inserted into the cardiovascular lumen. The temperature of the cardiovascular wall is measured with the temperature sensor, and the distance from the temperature sensor to the cardiovascular wall is determined. The cardiovascular wall temperature is adjusted based on the distance determination, and the vulnerable plaque is determined based on the adjusted wall temperature measurement.

19 Claims, 5 Drawing Sheets

INSTRUMENTED CATHETER WITH DISTANCE COMPENSATION TO SENSE VULNERABLE PLAQUE

RELATED APPLICATIONS

This application claims is a Division of and claims the benefit of U.S. patent application Ser. No. 10/692,145 filed Oct. 22, 2003, all of which are incorporated herein by reference.

FIELD OF THE INVENTION

This invention relates generally to the determination and location of vulnerable plaque. More specifically, the invention comprises a method and apparatus for measuring arterial wall temperature proximate the vulnerable plaque and to correct the measured temperature for distance to the arterial wall.

BACKGROUND OF THE INVENTION

The rupture of unstable or vulnerable atherosclerotic plaques located on the walls of coronary arteries, the carotid arteries, and other cardiovascular arteries, combined with associated thrombosis, is recognized as a common cause of acute coronary syndrome (ACS) such as unstable angina, myocardial infarction, and sudden ischemic cardiac death. Stabilization or reduction of vulnerable plaques motivates the current medical research in vulnerable plaque detection and treatment.

Vulnerable plaque is formed in the vessels of the heart and those supplying blood to the brain. It largely goes undetected, though its shape and composition make it susceptible to disruption, resulting in a blood clot that can cut the supply of blood to the heart or brain, producing chest pain, heart attack or stroke.

Vulnerable plaques are small lesions typically comprising a lipid-rich core, surrounded by a thin, collagenous cap with varying degrees of smooth muscle cells. The vulnerable plaques form within the walls of cardiovascular vessels, and are often eccentric in shape with irregular borders. The plaques may be characterized by a thickened arterial wall, partial stenosis, and generally elliptical distortion of the cardiovascular lumen with blockages ranging from zero up to about 70%. Stenoses are generally less severe with vulnerable plaques than stable plaques. However, mild stenoses are far more common and are responsible for more occlusions than tighter stenoses. Vulnerable plaques may be differentiated by their size, shape and composition of their lipid cores and fibrous caps. Acute lesions are larger with crescent-shaped cores rich in cholesterol esters with extracellular lipid accumulation. The fibrous cap may be infiltrated with macrophages throughout and at the borders in contact with normal intima, a precursor to a disruption of the vulnerable plaque initiated with mechanical strain or degradation of the wall thickness.

The fibrous cap may fatigue and rupture from mechanical stresses, releasing macrophages and tissue factor leading to thrombosis. Tension within the cap occurs with elevated blood pressure and larger vessel radius. Cyclical tension and compression of the cap occur with normal systolic-diastolic pressure changes that increase with faster heart rate and increased activity. Bodily movements and physical exertion may stress the plaque and exacerbate the onset of fissures in the cap. The cap may also degrade from the secretion of proteolytic enzymes such as plasminogen activators and metalloproteinases from lipid-filled macrophages (foam cells) resulting in plaque disruption and atherogenic vulnerability. The cap may be compromised by the presence of inflammation and swelling. As a result, activated inflammatory cells release heat that, when detected, indicates the presence and progression of vulnerable plaque.

Many devices have been proposed to detect vulnerable plaque. Magnetic resonance imaging, nuclear imaging techniques, endovascular ultrasonography, angiography, angioscopy, infrared spectroscopy, and cardiovascular wall temperature measurements may be used to determine the presence and location of carotid, aortic and coronary atherosclerotic plaques. Included in such devices are thermal sensing catheters, as well as infrared and optical coherence tomography (OCT) catheters.

Measurement of temperature differences between vulnerable plaques and normal vessels provides direct evidence of inflammatory material in the plaque core and thin walls surrounding the core. Normal arterial wall temperatures are relatively constant at about 0.65 degree centigrade above oral temperature; in contrast, the wall temperatures of patients with coronary artery disease of increasing severity have progressively larger deviations between the temperatures of the plaque lesions and the baseline wall, ranging from 0.1 to 0.2 degrees centigrade for stable angina to 1.25 to 2.65 degrees centigrade in those with acute myocardial infarction. Degradation of the cap thickness may further enhance the observable temperature differential, providing further indications of severity and impending peril. Plaque rupture may be predicted by looking for hot spots in arterial walls that are caused by the release of heat from the activated inflammatory cells.

To properly function, a temperature-sensing device often requires that the device be centered within the arterial lumen. Unfortunately, sensors of a device may be offset from the center of the artery and the artery itself may have eccentricity impacting the accuracy of the measurement. A sensor that moves with respect to the wall, such as to be periodically close or far away, may give imprecise temperature measurements, leading to an incorrect assessment of the vulnerable plaque.

Invasive procedures may provide the best opportunity for vulnerable plaque identification and local treatment. Such methods are conveniently used during angioplasty or other surgical procedures when the patient is undergoing intensive procedures involving catheters.

Instrumented catheters provide imagery and sensor information as the guidewire and catheter body are manipulated through the larger arterial vessels in the body. Often catheters are inserted into the femoral artery in the thigh and threaded up a circuitous path into the heart or through the carotid arteries and into the cerebellum. Cardiovascular wall temperatures may be extracted with thermocouple measurements from a suitably equipped guidewire. The thermocouple is tensioned with a graceful kink in the guidewire, providing direct contact with the lumen wall as the guidewire progresses through the vessels. Measurement accuracy is low due to the pulsing flow of blood in the vicinity of the thermocouple, which rapidly diffuses heat generated by the vulnerable plaque. Contact measurements present an intrinsic risk of generating fissures in the plaque wall and liberating its contents, while increasing the risk of thrombogenic responses and the potential for coronary failure.

Temperature measurements of the cardiovascular walls using intravascular, non-contact techniques are a desirable way to avoid undue traction with the vessel wall. Catheter-based apparatus may ascertain the presence and extent of vulnerable plaque, and allow for immediate, localized treatment of the atherosclerotic lesions. While non-contact, catheter-based diagnosis and treatment are attractive therapeutic methodologies for stabilization and abatement of vulnerable plaque, accurate determination of wall temperature is difficult due to the pulsating fluid flow through the vessel and around the temperature sensor. The amount of error in temperature measurement increases as a temperature sensor moves further from the vascular wall. Thermal imaging devices are similarly compromised due to varying opacities of the blood in the vessel. Compensation for errors introduced in the measurement of distance between the temperature sensor and the cardiovascular wall would increase the accuracy of the temperature measurements and provide a more accurate determination of the extent and severity of the vulnerable plaque.

The temperature of the cardiovascular fluid and the cardiovascular wall is affected by the rate of fluid flow in the vessel. Temperature variations due to flow are on the order of several tenths of a degree, and compensation of the temperature measurements with flow measurements would provide a more accurate measurement of cardiovascular wall temperature to determine the presence and progression of the vulnerable plaque. Natural pulsations of the blood within the cardiovascular vessel cause a rise and fall of the measured temperature. Blood flow within the vessel may have a significant effect on the temperature measurement and should be accounted for in temperature measurements.

It is an object of this invention, therefore, to provide a method and system for determining vulnerable plaque and other vascular conditions using improved temperature sensing, to provide an option for local treatment or long-term treatment of the vulnerable plaque, and to overcome the deficiencies and limitations described above.

SUMMARY OF THE INVENTION

One aspect of the invention provides a method of determining vulnerable plaque in a cardiovascular lumen. A guide member including a temperature sensor and a distance sensor are inserted into the cardiovascular lumen. The temperature of the cardiovascular wall is measured with the temperature sensor, and the distance from the temperature sensor to the cardiovascular wall is measured with the distance sensor. The cardiovascular wall temperature measurement may be adjusted based on the distance measurement, and the presence of the vulnerable plaque is determined based on the adjusted cardiovascular wall temperature measurement.

The baseline temperature of the cardiovascular lumen may be determined based on a plurality of adjusted cardiovascular wall temperature measurements. Each adjusted cardiovascular wall temperature measurement is compared to the baseline temperature, and the presence of the vulnerable plaque may be determined when the adjusted cardiovascular wall temperature measurement is above the baseline temperature by at least a predetermined threshold.

A measurement of fluid flow rate proximate the temperature sensor and the distance sensor may be made with a flow sensor coupled to the guide member. The cardiovascular wall temperature measurement may be adjusted based on the fluid flow rate measurement.

When the vulnerable plaque has been determined, the vulnerable plaque may be treated using one or more vulnerable plaque treatment methods. The treatment of vulnerable plaque may be more effective when the determination and location of the vulnerable plaque is more accurate.

An apparatus and a system for determining the vulnerable plaque in a cardiovascular lumen are also disclosed.

The aforementioned, and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

The present invention is illustrated by the accompanying drawings of various embodiments and the detailed description given below. The drawings should not be taken to limit the invention to the specific embodiments, but are for explanation and understanding. The foregoing aspects and other attendant advantages of the present invention will become more readily appreciated by the detailed description taken in conjunction with the accompanying drawings, wherein.

DETAILED DESCRIPTION OF THE PRESENTLY PREFERRED EMBODIMENTS

One aspect of the present invention is an instrumented catheter or guidewire to provide measurements of cardiovascular wall temperature and determine vulnerable plaque. Wall temperature is measured and compensated using a distance sensor for determining the distance between the temperature sensor and the vessel wall, and correcting the temperature measurement based on the distance determination. Alternatively, or additionally, the temperature measurement may be corrected with flow sensor measurements. A cardiac flow sensor may measure vessel blood flow. A guide member comprising a temperature sensor, a distance sensor and a flow sensor may be inserted into the cardiovascular lumen and used in combination to adjust the cardiovascular wall temperature for a more accurate vulnerable plaque location determination. The flow measurements may be used to synchronize the temperature measurement to a specific portion of the vessel flow cycle. Vulnerable plaque may be determined based on the adjusted temperatures.

Figure 1:
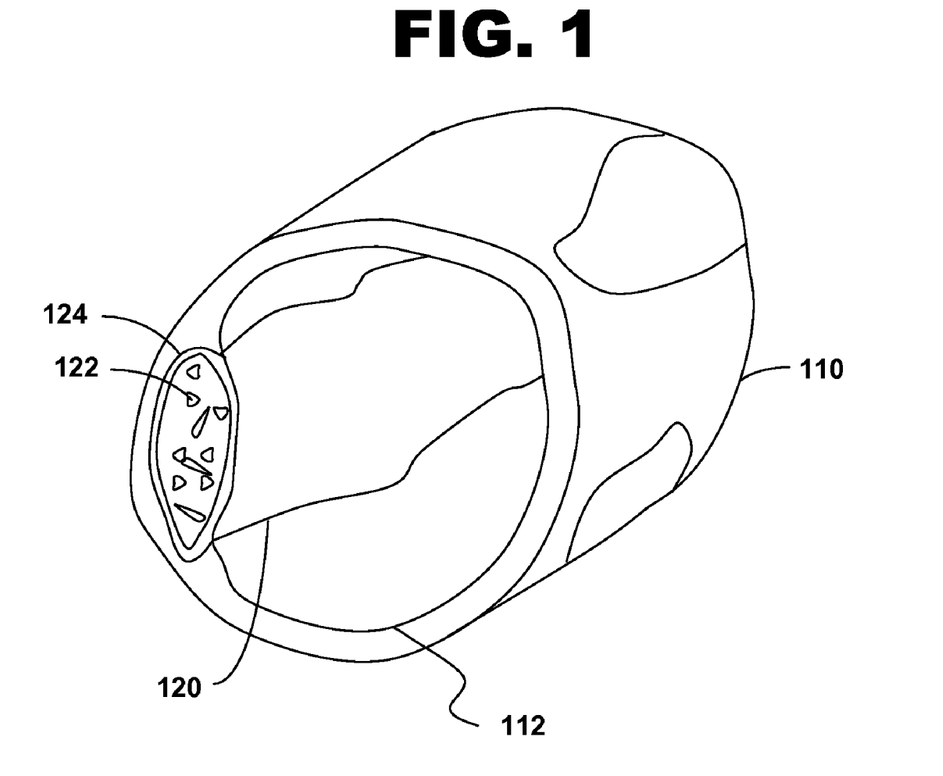
FIG. 1 is a pictorial illustration of a vulnerable plaque lesion lining the wall of a cardiovascular vessel.

FIG. 1 shows an illustration of a vulnerable plaque lesion lining the wall of a cardiovascular vessel at 100. A cardiovascular vessel 110 in the heart or leading from the heart or to the brain may be afflicted with vulnerable plaque 120. A soft, lipid core 122 surrounded by an irregular, fibrous cap 124 represents vulnerable plaque 120 within the cardiovascular wall 112. The vulnerable plaque may cause a partial stenosis of the blood vessel, causing local irregularities in the cross-sectional geometry of the artery. Blood and other bodily fluids pumping through the blood vessel cause mechanical stresses on the vascular wall and on the plaque. The blood flow and inflammation within the wall and core of the vulnerable plaque create variations in the temperature distribution across the blood vessel, depending on the severity of the vulnerable plaque and the proximity of the temperature sensor to the plaque.

Figure 2:
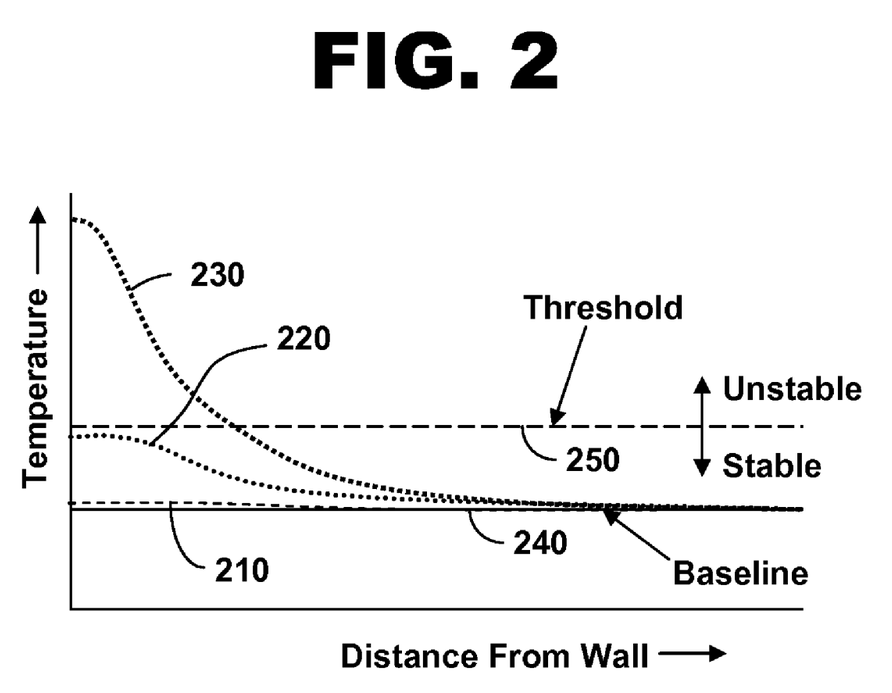
FIG. 2 is a graphical illustration of the temperature distribution from a cardiovascular wall to the center of the blood vessel indicating the presence of vulnerable plaque, in accordance with the current invention.

FIG. 2 shows a graphical illustration of the temperature distribution from a cardiovascular wall to the center of the blood vessel, in accordance with the present invention at 200. Inflammation associated with the vulnerable plaque generates heat and causes a higher wall temperature, the amount depending on the severity of the plaque, the thickness of the cap, and the heat flow dynamics associated with the flowing blood. In the absence of vulnerable plaque, the wall temperature and the blood temperature would be essentially the same from wall to wall through the bloodstream, as seen with normal temperature distribution curve 210. In the presence of stable plaque, the temperature at the cardiovascular wall may be slightly elevated, and then it rapidly drops to the normal bloodstream temperature at short distances from the wall, as seen with stable plaque temperature distribution curve 220. In cases of unstable or vulnerable plaque, the cardiovascular wall temperature may be much higher than the normal bloodstream temperature, and the temperature may rapidly drop with distance away from the wall, as shown with vulnerable plaque temperature distribution curve 230. The temperature distribution profiles may approach a baseline temperature 240. Notably, baseline temperature 240 may be quickly reached at positions upstream and downstream of the vulnerable plaque, and that the wall temperature may vary within a given vulnerable plaque lesion.

Vulnerable plaque may be determined when the wall temperature is above baseline temperature 240 by a predetermined threshold 250. Atherosclerotic plaque may be considered stable, for example, when the cardiovascular wall temperature is below the threshold, or considered to be vulnerable when the cardiovascular wall temperature is above predetermined threshold 250. As seen from the figure, an incorrect determination of plaque vulnerability may result when temperature measurements made in the bloodstream are not compensated with the distance from the vessel wall.

Figure 3:
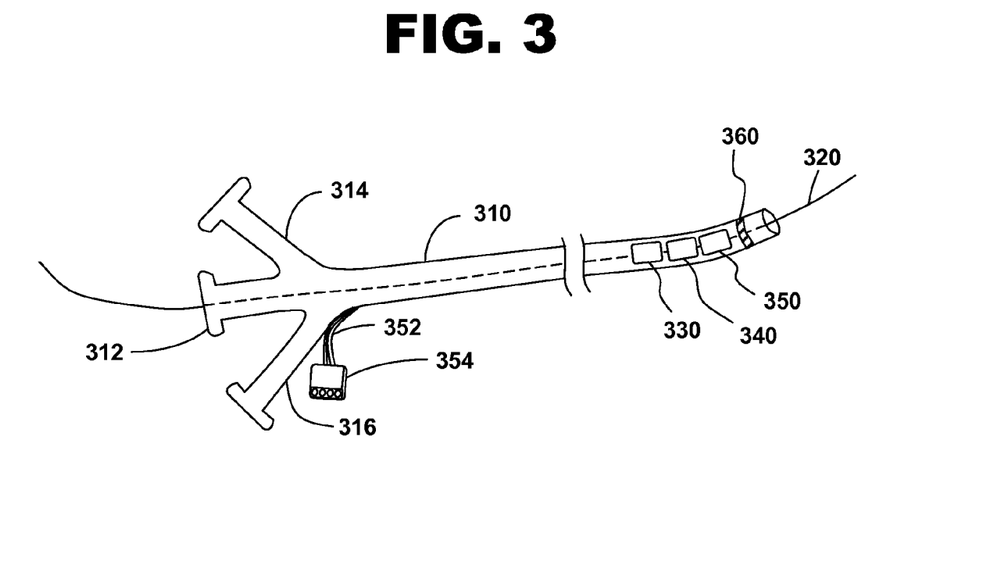
FIG. 3 is an illustration of a catheter instrumented with a temperature sensor, a distance sensor and an optional flow sensor, in accordance with the current invention.

FIG. 3 shows a catheter instrumented with a temperature sensor, a distance sensor and an optional flow sensor, in accordance with the present invention at 300. Typically, a catheter body 310 is a long, polymeric tube with a hollow interior, made from suitable biocompatible materials. The distal end of catheter body 310 has a hole for a guidewire 320. Guidewire 320 is typically of metallic construction, to provide the strength and flexibility required without kinking or collapsing. Before inserting catheter body 310, guidewire 320 may be inserted into the body through an incursion into, for example, the femoral artery in the leg or groin region. Guidewire 320 may be maneuvered through various vessels in the body by careful pushing and twisting, while the progress may be observed on an external viewer of an imaging system. As guidewire 320 is maneuvered throughout the body, catheter body 310 may be slipped over guidewire 320, and guided along the vascular route. Guidewire 320 and catheter body 310 may be slid further into the body, until the guidewire and catheter are at their desired locations. The distal end of catheter body 310 may include a balloon for angioplasty, a stent, or other implantable or treatment device (not shown). The proximal end of catheter body 310 has a guidewire port 312 for loading, handling, and withdrawing guidewire 320. The proximal end of catheter body 310 may also have a pressure port 314 for enlarging a balloon or for deploying a stent at the end of catheter body 310. Pressure port 314 may be fluidically coupled to the distal end of catheter body 310 through an annular region within the catheter body for enlarging the balloon or deploying the stent. Catheter body 310 may also have a pressure relief port 316 for relieving pressure in the annular region of catheter body 310.

Near the distal end of catheter body 310 are a temperature sensor 330 and a distance sensor 340. Temperature sensor 330 and distance sensor 340 may be mounted on the side of catheter body 310 or embedded in its polymeric casing. Alternatively, temperature sensor 330 and distance sensor 340 may be mounted at the distal end of catheter body 310. Temperature sensor 330 and distance sensor 340 normally point outwards from catheter body 310 to observe the wall of the encroached vessel. Two or more temperature sensors 330 and associated distance sensors 340 may be positioned about the circumference of catheter body 310, or as desired along the length of catheter body 310, or alternatively, on the distal tip of catheter body 310. Multiple temperature sensors and distance sensors may give more temperature measurements for improved profiling of the vulnerable plaque along the length and around the circumference of the vessel.

A flow sensor 350 or other sensors may also be mounted at or near the distal end of catheter body 310. Flow sensor 350 may be any suitable flow-sensing device for measuring fluid flow proximate temperature sensor 330 and distance sensor 340.

Temperature sensor 330 may be a thermocouple, a thermopile, a resistive temperature-sensing device (RTD), or any suitable temperature-sensing device for measuring elevated temperature areas on the vessel wall or in the surrounding blood. Temperature sensor 330 may comprise an infrared temperature detector such as a microbolometer for determining the vessel wall temperature. Due to the generally large absorption of infrared radiation by components in the blood, wall temperature measurements may use an infrared temperature detector with an optical passband corresponding to a region of transparency through bodily fluid within the cardiovascular lumen. Temperature measurements may be taken using relatively transparent regions or transmissive regions in the blood, such as through the windows extending from 1.4 to 1.8 microns, 2.1 to 2.4 microns, 3.7 to 4.3 microns, 4.6 to 5.4 microns, 7.0 to 14.0 microns, or other suitable wavelength bands close to the peak of the radiation curve at normal body temperatures.

Distance sensor 340 may comprise an optical sensor or an ultrasonic transducer. An optical sensor may use interferometric techniques or focusing techniques such as confocal imaging or other suitable imaging techniques to determine the distance from the temperature sensor to the vessel wall. An ultrasonic transducer would launch acoustic energy in short bursts towards the vessel wall and monitor the reflections. From the time delay between the launch and the echo, the distance from the temperature sensor to the vessel wall can be ascertained. Analysis of the ultrasonic signal may additionally be used to determine, for example, the cap thickness and pliability (stiffness) of the vulnerable plaque.

Depending upon the blood vessel selected, the cyclic variation of blood temperature may approach ±0.1 degree centigrade. Therefore, alternatively, flow sensor 350 may provide blood flow measurements via Doppler ultrasound or temperature sensing to alternatively, or additionally, compensate the temperature measurements for fluid flow through the cardiovascular vessel. Flow measurements may allow optimized temperature sensing by sampling the temperature at a specific point during each cardiac blood flow cycle, such as near a positive or negative peak of the flow cycle. In yet another alternative, the distance sensor 340 may also incorporate both distance and flow measurements.

Electrical connections to the temperature and distance sensors are made through catheter wiring 352 and catheter connector 354. Catheter wiring 352 extends from each of the sensors back to the proximal end of catheter body 310. Catheter wiring 352 may consist of multiple stranded or solid core wires with electrical insulation. Catheter wiring 352 may line the outside of catheter body 310, the interior of catheter body 310, or be embedded within the polymeric tubing. Catheter wiring 352 may be connected to catheter connector 354, which provides suitable strain relief and electrical coupling to external interface electronics.

Instrumented catheter body 310 may include a locator 360 for determining the position of the temperature sensor. Locator 360 may comprise a radiopaque marker, a radio-frequency coil, an ultrasonic marker transducer, or other means for location determination. Radiopaque markers are relatively opaque to X-rays and thus, produce an area of high contrast for external imaging. A radiopaque marker may be banded onto catheter body 310. The radiopaque marker may comprise an inert, noble metal such as gold, platinum, iridium, palladium, rhodium, or other opaque, biocompatible material. An X-ray imaging system or other suitable imaging system may be used to determine the position of the marker, from which the location of the temperature sensor and any detected vulnerable plaque may be determined.

Locator 360 may comprise a radio-frequency coil. The miniature coil may be mounted on or within the catheter body. Using external detection mechanisms and triangulation, such as described in U.S. Pat. No. 6,366,799, issued Apr. 2, 2002, the location of the coil and any vulnerable plaque may be determined.

Locator 360 may, alternatively, comprise an ultrasonic marker transducer. The transducer may be mounted on or within the catheter body. Using external detection mechanisms and triangulation, such as described in U.S. Pat. No. 5,840,030, issued Nov. 24, 1998, the location of the sensors and any vulnerable plaque may be determined.

Figure 4:
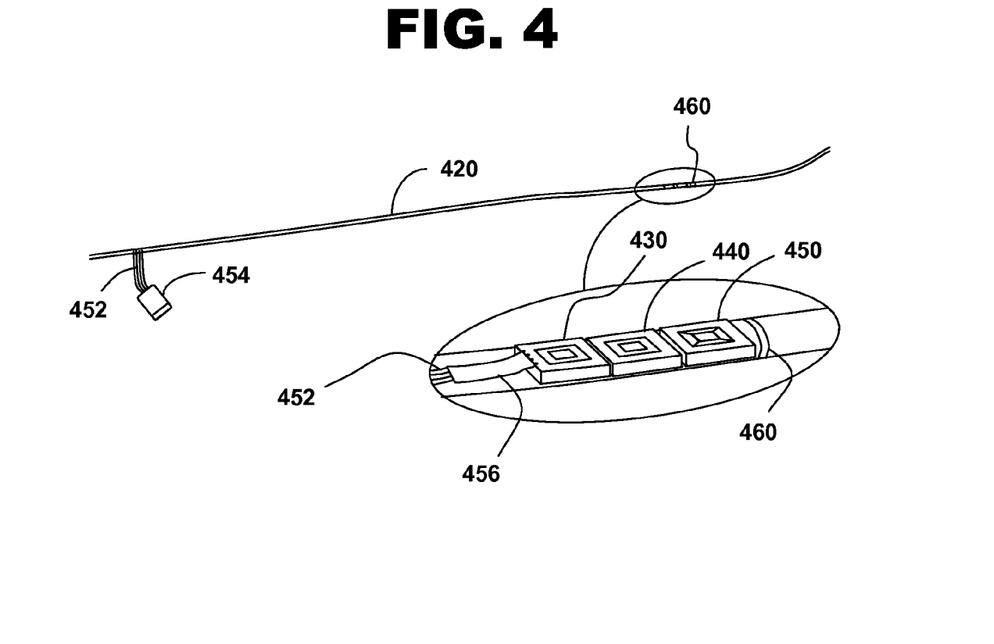
FIG. 4 is an illustration of a guidewire instrumented with a temperature sensor, a distance sensor and an optional flow sensor, in accordance with the current invention.

FIG. 4 shows a guidewire instrumented with a temperature sensor, a distance sensor and an optional flow sensor, in accordance with the present invention at 400. In this embodiment, one or more temperature sensors 430, distance sensors 440, and optional flow sensor 450 are mounted onto a guidewire body 420. Temperature sensor 430 and distance sensor 440 may be adhered to guidewire body 420 using any suitable epoxy or bonding means. Temperature sensor 430, distance sensor 440, and optional flow sensor 450 may be housed in one or more packages that are mounted to guidewire body 420.

An interconnect cable 456 such as thin, copper or metallic traces on a polyimide tape may be used to connect temperature sensor 430, distance sensor 440, and optional flow sensor 450 to a guidewire wiring 452 and a guidewire connector 454. Guidewire wiring 452 may comprise a ribbon cable or a bundle of insulated wires attached to guidewire body 420. Guidewire connector 454 provides suitable strain relief and electrical coupling to external interface electronics.

Instrumented guidewire body 420 may include a locator 460 for determining the position of the temperature sensor. Locator 460 may comprise a radiopaque marker, a radio-frequency coil, an ultrasonic marker transducer, or other location determination device. The radiopaque marker, comprising an inert, noble metal such as gold, platinum, iridium, palladium, rhodium, or other suitably opaque, biocompatible material may be banded onto guidewire body 420. An X-ray imaging system or other suitable imaging system may be used to determine the position of the marker and thereby determine the location of any detected vulnerable plaque. Alternatively, locator 460 may comprise a radio-frequency coil. The miniature coil may be mounted on guidewire body 420. Using external detection mechanisms and triangulation, the location of the coil and any vulnerable plaque may be determined. Alternatively, locator 460 may comprise an ultrasonic marker transducer. The miniature transducer may be mounted on guidewire body 420. Using external detection mechanisms and triangulation, the location of the transducer and any vulnerable plaque may be determined.

Figure 5:
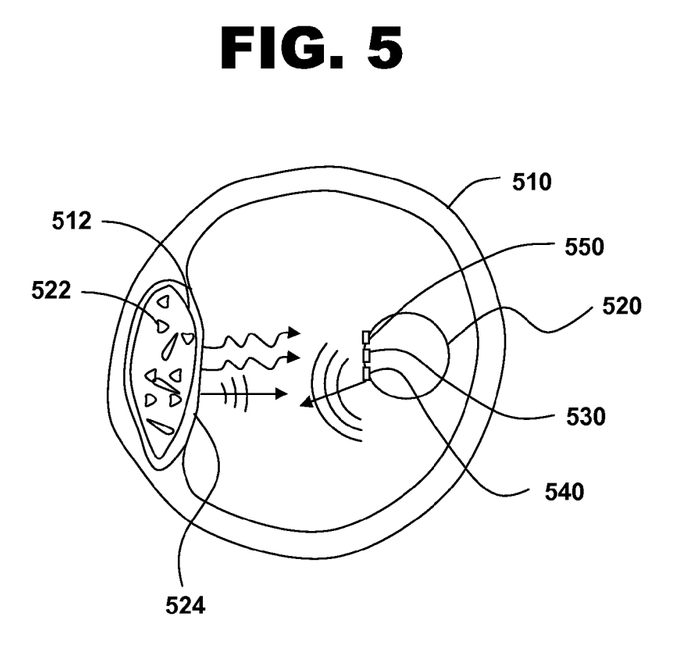
FIG. 5 is a cross-sectional view of an instrumented catheter or guidewire inside an afflicted blood vessel, in accordance with the current invention.

FIG. 5 shows a cross-sectional view of an instrumented guide member inside an afflicted blood vessel, in accordance with the present invention at 500. A guide member 520 may comprise an instrumented catheter or an instrumented guidewire. Instrumented guide member 520 may be positioned internal to cardiovascular lumen 510. Guide member 520 may be relatively centered in the vascular lumen, or may be close to or in contact with any portion of the cardiovascular wall 512. Its position may vary with the pulsation of bodily fluid and machinations of guide member 520 as it is pushed, pulled, and twisted through various blood vessels within the body.

Vulnerable plaque with a soft, lipid-filled core 522 and a fibrous cap 524 is illustrated as residing on the wall of cardiovascular lumen 510. Instrumented guide member 520 containing a guide member temperature sensor 530 and a distance sensor 540 is positioned near the vulnerable plaque. An optional flow sensor 550 is located near temperature sensor 530 and distance sensor 540. Temperature measurements are taken with an RTD, thermocouple, thermopile, infrared detector or any suitable temperature sensing means. Distance measurements are made using an optical sensor, an ultrasonic sensor, or any suitable distance sensing means. Distance measurements are used to offset, adjust or compensate the temperature measurements for determining accurate lumen wall temperatures. Flow measurements may be used to adjust or compensate the temperature measurements for increasing the accuracy of the temperature measurements, or to determine points during each cardiac flow cycle at which the temperature measurements should be taken.

Figure 6:
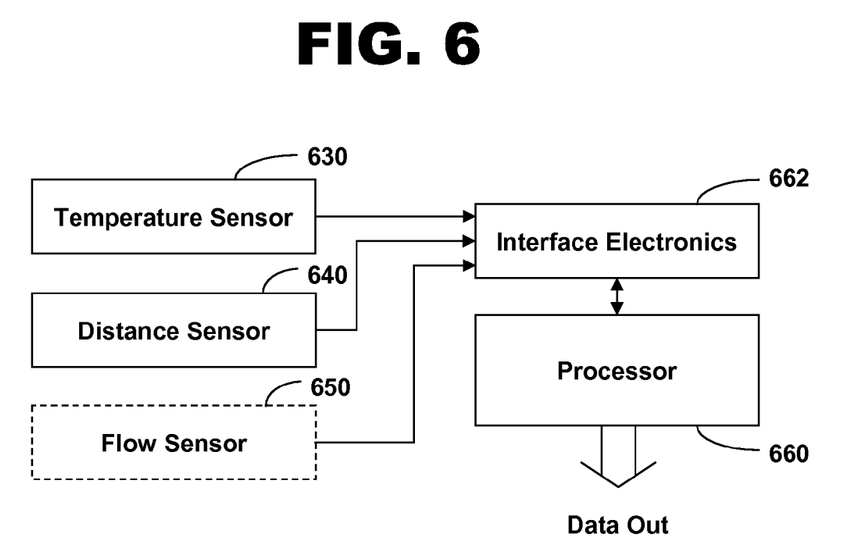
FIG. 6 is a block diagram of one embodiment of a system for determining vulnerable plaque in a cardiovascular lumen, in accordance with the current invention.

FIG. 6 shows a block diagram of one embodiment of a system for determining vulnerable plaque in a cardiovascular lumen, in accordance with the present invention at 600. Vulnerable plaque determination system 600 comprises one or more temperature sensors 630, one or more distance sensors 640, one or more digital signal processor 660, and interface electronics 662. The temperature sensors, distance sensors and optional flow sensors 650 are located on a guidewire or a catheter. The instrumented guidewire or catheter is inserted into the body, and cardiovascular wall temperatures may be taken with temperature sensor 630 using interface electronics 662. Interface electronics 662 may include suitable amplifiers, signal conditioning circuits and analog-to-digital converters for biasing the temperature sensors and extracting a temperature measurement. Distance measurements may be taken with distance sensor 640 and interface electronics 662. Interface electronics 662 may also include suitable amplifiers, signal conditioning circuits and interface circuits for driving the distance sensor and extracting a distance measurement. Flow measurements may be taken with flow sensor 650 and interface electronics 662. Interface electronics 662 may also include suitable amplifiers, signal conditioning circuits and interface circuits for driving the flow sensor and extracting a flow measurement. Using processor 660, the temperature measurements may be adjusted based on the distance determination and/or blood flow determination, and vulnerable plaque may be determined based on the adjusted cardiovascular wall temperature measurements. Processor 660 may be a microcontroller, a microprocessor, a central processing unit (CPU), a host computer, a personal computer (PC), a networked computer, or any device capable of processing the measured data. Computer program code may provide instructions for processor 660 using any suitable programming language and computer readable medium.

Processor 660 may take multiple temperature, distance, and blood flow measurements as the instrumented guide member is moved throughout the vessel. These multiple adjusted cardiovascular wall temperature measurements are used to determine a baseline temperature indicative of the background or normal temperature of the cardiovascular lumen. Processor 660 may compare each adjusted temperature measurement to the baseline temperature and determine vulnerable plaque when the adjusted cardiovascular wall temperature measurement is above the baseline temperature by at least a predetermined threshold.

Figure 7:
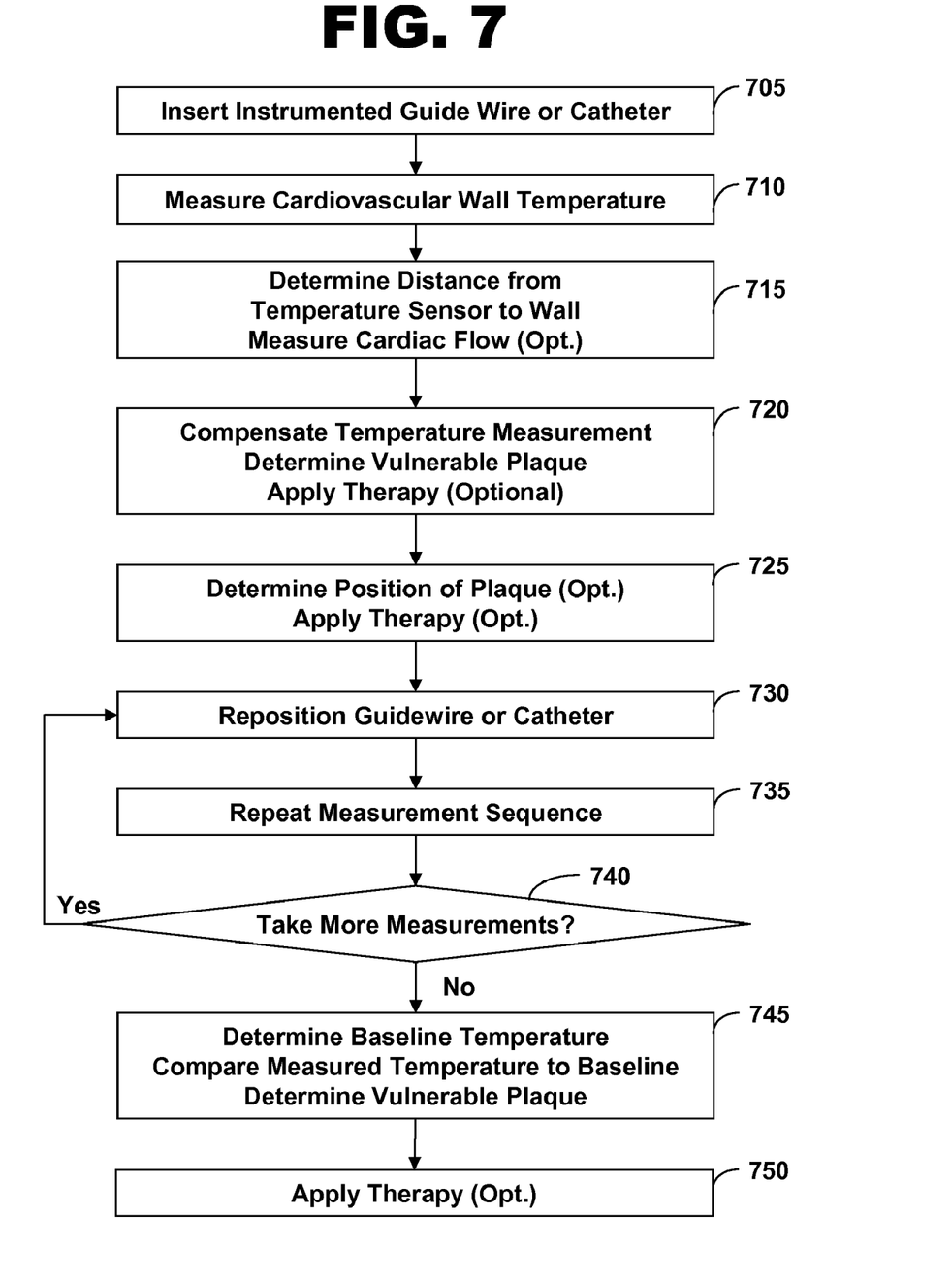
FIG. 7 is a flow diagram of one embodiment of a method for determining vulnerable plaque in a cardiovascular lumen, in accordance with the current invention.

FIG. 7 shows a flow diagram of one embodiment of a method for determining vulnerable plaque in a cardiovascular lumen, in accordance with the present invention at 700.

Vulnerable plaque determination method 700 begins by inserting an instrumented guide member such as an instrumented guidewire or an instrumented catheter into a cardiovascular lumen, as seen at block 705. The instrumented guidewire or catheter may include one or more temperature sensors one or more distance sensors, and one or more blood flow sensors operably coupled to the guide member. The distance sensor may be coupled proximate the temperature sensor to provide measurements of the distance from the temperature sensor to the cardiovascular wall for compensating the cardiovascular wall temperature measurements. The flow sensor may be used to measure blood flow through the vessel and to compensate the temperature measurements, or to synchronize the temperature measurement to a specific location on the blood pressure flow cycle such as at the positive or negative peak of the flow cycle. It should be understood that throughout this specification, a measurement of temperature, distance or flow may or may not be in calibrated units and may or may not be converted into an actual calculated temperature, distance or flow. The outputs of any of the sensors may be utilized directly in providing the desired inputs for compensating the temperature measurements. Alternatively, the outputs of any of the sensors may be converted into digital signals and used to calculate the adjusted cardiovascular wall temperatures. Vulnerable plaque determinations may be determined with any combination of amplified or un-amplified, linearized or non-linearized, formatted or unformatted signals.

The temperature sensor, as seen at block 710, may measure the cardiovascular wall temperature. The distance sensor may determine the distance from the temperature sensor to the cardiovascular wall, as seen at block 715. The optional flow sensor may be used to measure the cardiac flow or fluid flow rate through the cardiovascular vessel near the temperature sensor and the distance sensor, as seen at block 715. The temperature measurement may be offset or compensated by the distance measurement and any fluid flow measurements to provide an adjusted cardiovascular wall temperature, as seen at block 720. A determination may be made of vulnerable plaque on the vessel wall, based on the adjusted temperature measurement, and a local treatment may be applied optionally. The position of the plaque may be optionally determined, as seen at block 725. When vulnerable plaque is present, a treatment may optionally be applied. The treatment may include a vulnerable plaque therapy, where a patient may take medication such as statin therapy over extended periods of time. The treatment may include immediate application of therapeutic drugs to the vulnerable plaque using, for example, a catheter-based drug delivery method. Alternatively, the treatment may include determining the position of the vulnerable plaque, then removing the instrumented catheter or guidewire and replacing it with another catheter or guidewire with the capability for treating the vulnerable plaque. For example, the treatment may include intravascular delivery of therapeutic compounds at the determined location while the patient remains in surgery. Determination of the position of the vulnerable plaque may include using an imaging system in conjunction with a radiopaque marker or a radio-frequency coil of wire attached to the instrumented guide member. Plaque location determination may be beneficial for evaluating progress in treatment of the plaque during subsequent observations and future procedures.

Additional measurements may be made by repositioning the guide member, as seen at block 730. The measurement sequence may be repeated, as seen at block 735. Temperature and distance measurements may be taken, and an adjustment made to the temperature measurements based on the distance determination. Vulnerable plaque may be determined and treated locally, or the position of the plaque may be determined and a suitable treatment method initiated. This sequence may be repeated as often as needed, as seen at block 740.

When a sufficient number of measurements have been taken, a baseline temperature may be determined, as seen at block 745. The average of all the adjusted temperature measurements may be made, or a grouping of the lowest adjusted temperature measurements may be used to determine the baseline temperature of the cardiovascular lumen wall. Each adjusted temperature measurement may be compared to the baseline temperature, and a determination made of the presence, extent and severity of any vulnerable plaque. A predetermined threshold may be used to determine the vulnerable plaque. For example, when an adjusted temperature measurement is above the baseline temperature by a predetermined amount, the plaque may be considered vulnerable and treatment may ensue.

Therapy may be applied to the vulnerable plaque, as seen at block 750. A local therapeutic treatment may be applied immediately when the instrumented catheter or guidewire is suitably equipped for treating the vulnerable plaque. In another embodiment of the present invention, the position of the vulnerable plaque may be determined, and another catheter inserted to apply the treatment. In yet another embodiment of the present invention, the instrumented catheter or guidewire may be extracted and a regimen of medication prescribed to stabilize or reduce the vulnerable plaque.

Although the present invention applies to the detection and treatment of vulnerable plaque, other cardiovascular and endovascular conditions may be accorded similar analysis and treatment.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A method of determining vulnerable plaque in a cardiovascular lumen, comprising:
   inserting a guide member into the cardiovascular lumen, the guide member including a temperature sensor and a distance sensor;
   measuring a cardiovascular wall temperature with the temperature sensor;
   determining a distance from the temperature sensor to the cardiovascular wall with the distance sensor;
   adjusting the cardiovascular wall temperature measurement based on the distance determination; and
   determining the vulnerable plaque based on the adjusted cardiovascular wall temperature measurement.

2. The method of claim 1 wherein the guide member is a catheter.

3. The method of claim 1 wherein the guide member is a guidewire.

4. The method of claim 1 wherein the temperature sensor comprises a resistive temperature device.

5. The method of claim 1 wherein the temperature sensor comprises a thermocouple or a thermopile.

6. The method of claim 1 wherein the temperature sensor comprises an infrared detector.

7. The method of claim 6 wherein the infrared detector has an optical passband corresponding to a region of transparency through bodily fluid within the cardiovascular lumen.

8. The method of claim 7 wherein a wavelength within the region of transparency ranges between 3.7 microns and 4.3 microns or between 4.6 microns and 5.4 microns.

9. The method of claim 1 wherein the distance sensor comprises an optical sensor.

10. The method of claim 1 wherein the distance sensor comprises an ultrasonic transducer.

11. The method of claim 1 further comprising:
    determining a baseline temperature of the cardiovascular lumen wall based on a plurality of adjusted cardiovascular wall temperature measurements;
    comparing each adjusted cardiovascular wall temperature measurement to the baseline temperature; and
    determining the vulnerable plaque when the adjusted cardiovascular wall temperature measurement is above the baseline temperature by at least a predetermined threshold.

12. The method of claim 1 further comprising:
    measuring a fluid flow rate proximate the temperature sensor and the distance sensor with a flow sensor coupled to the guide member; and
    adjusting the cardiovascular wall temperature measurement based on the fluid flow rate measurement.

13. The method of claim 1 further comprising:
    applying a therapy for the vulnerable plaque.

14. The method of claim 1 further comprising:
    determining a position of the vulnerable plaque; and
    treating the vulnerable plaque.

15. The method of claim 14 wherein the position of the vulnerable plaque is determined by a radiopaque marker on the guide member.

16. The method of claim 14 wherein the position of the vulnerable plaque is determined by a radio frequency coil attached to the guide member.

17. The method of claim 14 wherein the position of the vulnerable plaque is determined by an ultrasonic marker transducer coupled to the guide member.

18. An apparatus for determining vulnerable plaque comprising:
    a temperature sensor operably coupled to a guide member; and
    a distance sensor operably coupled to the guide member proximate the temperature sensor; wherein a measurement of a cardiovascular wall temperature is compensated by a measurement of a cardiovascular wall distance to determine the vulnerable plaque based on the compensated temperature measurement.

19. The apparatus of claim 18 further comprising:
    a flow sensor operably coupled to the guide member proximate the temperature sensor and the distance sensor; wherein the measurement of the cardiovascular wall temperature is compensated by a measurement of a fluid flow rate.

* * * * *